United States Patent [19]

Banasiak

[11] 4,247,417

[45] Jan. 27, 1981

[54] CATALYST FOR OLEFIN DISPROPORTIONATION

[75] Inventor: Dennis S. Banasiak, Bartlesville, Okla.

[73] Assignee: Phillips Petroleum Company, Bartlesville, Okla.

[21] Appl. No.: 57,246

[22] Filed: Jul. 11, 1979

[51] Int. Cl.³ .................... B01J 31/02; B01J 31/12
[52] U.S. Cl. ................... 252/429 R; 252/431 R; 252/431 P; 252/431 N; 585/645
[58] Field of Search ........... 252/429 R, 431 R, 431 P, 252/431 N; 585/645

[56] References Cited

U.S. PATENT DOCUMENTS

| | | | |
|---|---|---|---|
| 3,637,893 | 1/1972 | Singleton | 585/645 |
| 3,689,433 | 9/1972 | Kroll | 252/429 R |
| 4,024,201 | 5/1977 | Takahashi | 585/645 |

FOREIGN PATENT DOCUMENTS 773544  4/1972  Belgium .............. 252/429 R

OTHER PUBLICATIONS

J. C. S. Chem. Comm. pp. 1202-1203 (1971).

*Primary Examiner*—John F. Niebling

[57] ABSTRACT

A disproportionation of olefins is disclosed which employs a novel catalyst system consisting essentially of (I) at least one neutral carbene complex and (II) at least one chlorinated or chlorobrominated saturated organic compound containing only carbon and chlorine or carbon, chlorine, and bromine.

10 Claims, No Drawings

CATALYST FOR OLEFIN DISPROPORTIONATION

This invention relates to the disproportionation of olefins. More specifically this invention relates to a novel catalyst system and a novel process for the disproportionation of olefins.

The disproportionation or metathesis of olefins is a reaction in which one or more olefinic compounds are transformed into other olefins of different molecular weights. The disproportionation of an olefin to produce one olefin of a higher molecular weight and one olefin of a lower molecular weight can also be referred to as a self-disproportionation. For example, propene can be disproportionated to ethylene and cis- and trans-2-butene. Another type of disproportionation involves the codisproportionation of two different olefins to form still other olefins. For example, the reaction of one molecule of 2-butene with one molecule of 3-hexene can produce two molecules of 2-pentene.

Several catalyst systems have been proposed for the disporportionation of olefins. Several disadvantages have been observed for these catayst systems. In some cases, isomerization of the double bond of the starting material or product occurs and disproportionation involving the isomeric olefin yields a mixture of products which is difficult to separate. With certain catalysts, polymerization of the olefins occurs at long reaction times or high reaction temperatures. Some catalysts cause alkylation of aromatic solvents with the olefin, thereby consuming some of the reactant or product and producing a more complex product mixture. Some catalysts are only effective for terminal olefins and other catalysts may be effective only with internal olefins. Many of the metathesis catalyst systems use organoaluminum compounds which are expensive and present operational difficulties during production, storage, and use.

An object of the present invention is to provide a novel disproportionation catalyst which produces very little undesirable olefin isomerization and which does not require the employment of expensive organoaluminum components.

Another object of the present invention is to provide a process for the disproportionation of olefins.

Other objects, features and advantages of the present invention will appear more fully from the following description.

SUMMARY OF INVENTION

In accordance with the instant invention, olefins can be disproportionated using a novel homogeneous catalyst consisting essentially of (1) at least one neutral carbene-metal complex and (2) at least one chlorinated or chlorobrominated saturated organic compound containing only carbon, chlorine, and bromine.

THE CATALYST SYSTEM

The carbene complex component of the catalyst system of this invention is a neutral, i.e., non-ionic, carbene complex having the general formula I

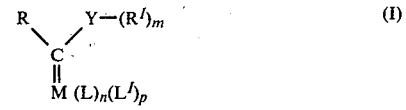

wherein R is an aryl or substituted aryl radical containing from 6 to about 30 carbon atoms per radical and with the aryl substituents being one or more or a mixture selected from a group consisting of halides, alkoxides, and alkyl radicals containing 1 to 20 carbon atoms per radical, $R^I$ is selected from a group consisting of alkyl, cycloalkyl, aryl, substituted aryl, trialkylsilyl, or triarylsilyl radicals containing from 1 to 30 carbon atoms per radical with the aryl substituents being the same as for R described above, Y is O, Se, S, N, or P, m is 1 when Y is O, Se, or S and m is 2 when Y is N or P, M is tungsten or rhenium, each L is a neutral ligand individually selected from the group consisting of Co, NO, $PF_3$, $PCl_3$, and pyridine, $L^I$ is cyclopentadienyl or allyl, and p is 0 or 1, and when p is 0 n is 5 and when p is 1 n is 2. Mixtures of ligand L can be used if desired. Specific examples of neutral carbene complexes include (methoxyphenylcarbene)pentacarbonyltungsten(O), (p-chlorophenylmethoxycarbene)pentacarbonyltungsten(O), (p-methylphenylmethoxycarbene)pentacarbonyltungsten(O), (p-methoxyphenylmethoxycarbene)-pentacarbonyltungsten(O), (phenoxyphenylcarbene)-pentacarbonyltungsten(O), (cyclohexyloxyphenylcarbene)pentacarbonyltungsten(O), (butoxyphenylcarbene)pentacarbonyltungsten(O), (octyloxyphenylcarbene)pentacarbonyltungsten(O), (hexadecyloxyphenylcarbene)pentacarbonyltungsten(O), (eicosyloxyphenylcarbene)pentacarbonyltungsten(O), (phenyltrimethylsiloxycarbene)pentacarbonyltungsten(O), (phenyltriphenylsiloxycarbene)pentacarbonyltungsten(O), (methylthiophenylcarbene)pentacarbonyltungsten(O), (dimethylaminophenylcarbene)pentacarbonyltungsten(O), (methoxyphenylcarbene)pentanitrosyltungsten(O) and corresponding rhenium carbenes. Mixtures of carbene complexes can be used if desired.

The presently preferred catalysts are those of formula I wherein R is a phenyl radical, Y is oxygen, $R^I$ is an alkyl radical containing 1 to about 10 carbon atoms per radical, m is 1, L is CO or No, n is 5, and p is 0.

For reasons of ease of preparation and reactivity, the currently most preferred carbene complex is

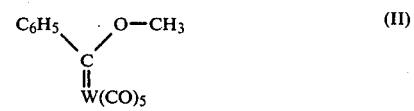

wherein $C_6H_5$ is a phenyl group.

The carbene complexes can be prepared by any of several published procedures, for example: D. J. Cardin, et al, Chem. Rev., 72, 545 (1972). D. J. Cardin, et al, Chem. Soc. Rev., 2, 99 (1973). C. P. Casey, in "Transition Metal Organometallic in Organic Synthesis", Vol. 1, H. Alper, Ed., Academic Press, 1976, pp. 189–233. "Inorganic Synthetis" Vol. 17, 95–99 (1979). In a typical preparation, carbene complex II is prepared by reacting tungsten hexacarbonyl with phenyllithium and then with the trimethyloxonium tetrafluoroborate.

The second component of the catalyst system of this invention can be termed a promoter or activator for the carbene complex and is a saturated organic compound which contains from 1 to 20 carbon atoms per molecule and contains only carbon and chlorine or only carbon, chlorine, and bromine. As will be demonstrated in the following examples, the presence of carbon-hydrogen bonds, aryl radicals, oxygen, carbon-carbon double bonds, and totally brominated structures have been found to be detrimental to the disproportionation of olefins.

Examples of suitable activators include carbon tetrachloride, bromotrichloromethane, hexachloroethane, dibromodichloromethane, chlorotribromomethane, tribromotrichloroethane, octachloropropane, octachlorocyclobutane, and the like. Mixtures of these activators can be used if desired.

The activator and the carbene complex are combined in any catalytically active amounts. The ratio of the catalyst components can be expressed in terms of a molar ratio of activator to carbene complex. The molar ratio of activator component to carbene component in the present invention can vary somewhat depending upon the activator selected. Generally, for all activators except carbon tetrachloride, the molar ratio of activator to carbene component is from about 1/1 to about 1000/1 and preferably from about 5/1 to about 100/1. For carbon tetrachloride as activator, the molar ratio of activator to carbene is generally from about 20/1 to about 1000/1 and preferably from about 30/1 to about 500/1.

The catalyst of the present invention is employed in a catalytically effective amount. The amount of catalyst employed in the process of this invention can be expressed in terms of the molar ratio of olefin to carbene complex component. Generally, the molar ratio of olefinic reactant to carbene component is from about 1/1 to about 5000/1 and preferably from about 50/1 to about 500/1.

OLEFIN REACTANTS

The process of this invention involves the contacting of two non-conjugated olefinic reactants, which may be the same olefin or different olefins, in the presence of the catalyst system described above. It is considered that the catalyst of this invention is generally suitable for the disproportionation of any of the olefins that are disproportionated by earlier conventional techniques. Typically, at least one of the olefinic reactants contains 3 to 30 carbon atoms per molecule and contains one or more carbon-carbon double bonds.

Generally, at least one of the olefinic reactants contains one or two non-conjugated carbon-carbon double bonds and is either an acyclic olefin represented by the formula III

$$R^{II}CH=CHR^{III} \qquad (III)$$

wherein $R^{II}$ and $R^{III}$ are independently selected from a group consisting of hydrogen, alkyl radicals, and alkenyl radicals with each of the radicals containing 1 to 18 carbon atoms per radical, or a monocyclic olefin represented by the following formula IV:

(IV)

wherein $R^{IV}$ is an alkylene or alkenylene radical containing 5 to 16 carbon atoms and wherein each of the radicals $R^{II}$, $R^{III}$, and $R^{IV}$ can contain one or more halides, e.g., chloride, bromide, provided the halides are at least two carbons from the carbons of the olefinic bond, and each of the radicals can contain one or more aryl or alkyl-substituted aryl groups, provided the aryl or alkyl-substituted aryl radicals are at least one carbon from the carbons of the olefinic bond.

For reasons of availability and reactivity, the currently preferred olefinic reactants are those of general formula III wherein $R^{II}$ and $R^{III}$ are selected from hydrogen and hydrocarbyl alkyl radicals containing 1 to 10 carbon atoms per radical.

Examples of suitable acyclic olefinic reactants include propene, 1-butene, 1-pentene, 2-pentene, 1-hexene, 2-hexene, 1-octene, 2-octene, 4-methyl-1-heptene, 2-decene, 6-dodecene, 1-tetradecene, 1-eicosene, 1,4-hexadiene, 4-chloro-1-butene, 4-phenyl-1-butene, and 4-phenyl-1-octene. Examples of suitable monocyclic olefins include cycloheptene, cyclooctene, cyclononene, cyclotetradecene, 4-chloro-1-cyclooctene, 1,5-cyclododecadiene, and 1,6-cyclodecadiene.

When two different olefinic reactants are utilized in the disproportionation, one of the olefins generally must be an acyclic or monocyclic olefin as described above and the other olefin can be either another acyclic or monocyclic olefin as described above or can be ethylene, a monocyclic monoolefin containing 4 to 6 carbons in the ring; e.g., cyclobutene, cyclopentene, and cyclohexene; or polycyclic mono- or diolefins. Examples of suitable polycyclic olefins include bicyclo[2.2.2]oct-2ene, bicyclo[2.2.2]oct-2,5-diene, bicyclo[2.2.1]hept-2-ene, and bicyclo[3.3.0]oct-2-ene.

When two different olefinic reactants are employed in the disproportionation process, the molar ratio of one olefinic reactant to the other olefinic reactant is not critical, and generally up to a 20-fold excess, preferably up to a 2-fold excess of one olefinic reactant can be employed.

REACTION CONDITIONS

The disproportionation reaction of this invention can be carried out under any suitable reaction conditions. Generally, the reaction is carried out at temperatures in the range of about 35° C. and about 200° C. While lower temperatures can be used, the reaction rates are generally too low to be of interest. Temperatures above 200° C. can be used, but excess decomposition of the reaction components can occur. Also, the higher reaction temperatures can result in some chlorination of the olefin reactants. The preferred reaction temperatures are from about 50° C. to about 100° C.

The pressure during the disproportionation reaction is generally in the range of about atmospheric to about 1500 psig (10341 kiloPascals gauge-kPa). Preferably, the pressure is in the range of about atmospheric to about 500 psig (3447 kPa).

The disproportionation can be carried out using a basically inert diluent or diluents such as saturated hydrocarbons, e.g., hexane, octane, cyclohexane, aromatic hydrocarbons, e.g., benzene, toluene, or halogenated compounds, e.g., chlorobenzene, chloroform, methylene chloride, bromoform can be used. Many of the activators can serve as the sole diluents at the upper ends of the ranges described for said activators. The amount of basically inert diluent employed can be expressed as a volume ratio of diluent to the activator portion of the catalyst system. Generally suitable volume ratios of diluent to activator are in the range of about 0/1 to about 500/1 and preferably about 1/1 to about 100/1.

The presence of oxygen and water has been found to be deleterious to the disproportionation reaction and should be substantially avoided during the reaction. Inert gases such as nitrogen or helium can be used to maintain a dry, inert atmosphere during the reaction.

The reaction time period depends on the reaction temperature and pressure as well as on the nature of the particular catalyst system and olefinic reactant used. The reaction time is generally from about 30 minutes to several days. Preferably the reaction time is from about 5 to about 100 hours.

REACTION PRODUCT WORKUP

The reaction product mixture from the disproportionation can be worked up using any combination of conventional separation and purification techniques. Depending on the relative volatilities of the unreacted starting olefins, the olefin products, the diluent (if used), and the chlorinated or chlorobrominated hydrocarbon activator can usually be separated by fractional distillation. The unreacted starting olefin, diluent, and activator can be recycled to the reaction zone. The olefin products can be purified by conventional techniques such as crystallization, distillation, or extractions.

The carbene catalyst can be removed, if desired, by the addition of dilute aqueous ammonium to decompose and precipitate the catalyst, followed by filtration and extraction. The resultant organic layer can be then worked up in a conventional manner.

REACTION PRODUCTS

According to the process of this invention, two olefinic reactants are disproportionated to form a product containing one or two olefins having a total number of carbon atoms equal to the sum of the carbon atoms of the two olefinic reactants and having a number of ethylenic double bonds equal to the sum of the ethylenic double bonds of the reactants.

One variation of the process comprises the disproportionation of two molecules of the same olefinic reactant. The reaction of two molecules of an acyclic olefin of formula III generally produces one olefin of a higher carbon number and one olefin of a lower carbon number as depicted in equation (1)

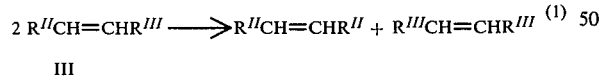

wherein $R^{II}$ and $R^{III}$ have the previously stated significance. If $R^{II}$ and $R^{III}$ represent identical groups, the disproportionation reaction will not cause any skeletal changes as the products $R^{II}CH=CHR^{II}$ and $R^{III}CH=CHR^{III}$ will be equivalent to $R^{III}CH=CHR^{II}$. By way of specific illustration, the reaction of two molecules of propylene produces ethylene and 2-butene. However, the reaction of two molecules of 2-butene produces two molecules of 2-butene. The reaction of two molecules of a cyclic olefin of formula IV produces a single cyclic diolefin. At high dilution the cyclic diolefin can be isolated, but in more concentrated solutions, further disproportionation frequently occurs to form materials of higher molecular weight. By way of specific illustration, the reaction of two molecules of cyclooctene in a dilute reaction mixture produces 1,9-cyclohexadecadiene.

Another variation of the process comprises the disproportionation of two different acyclic olefinic reactants. By way of specific illustration, the reaction of 2-butene and 3-hexene produces two molecules of 2-pentene and the reaction of propene with isobutene produces one molecule of isopentene and one molecule of ethylene.

Still another variation of the process is "ring-opening" disproportionation wherein an acyclic olefinic reactant (III) is contacted with a cyclic olefinic reactant (IV). The product of "ring-opening" is a single olefinic compound with one less carbocyclic ring than in IV, e.g., as depicted in equation (2).

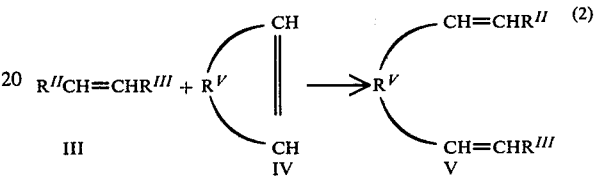

wherein $R^{II}$ and $R^{III}$ are as previously defined and $R^{V}$ is an alkylene or alkenylene radical containing 4 to 16 carbon atoms. By way of specific illustration, from reaction of 2-butene and cyclopentene is produced 2,7-nonadiene. Other typical products include 2,8-decadiene produced by reaction of cyclohexene and 2-butene, 3,8-undecadiene produced from 3-hexene and cyclopentene, 1,5,9-decatriene produced by reaction of ethylene and 1,5-cyclooctadiene, and 1,4-divinylcyclohexane from ethylene and bicyclo[2.2.2]oct-2-ene.

PRODUCT UTILITY

The olefinic products, for the most part, have established utility as precursors of polymers, e.g., as the third component of ethylene-propylene terpolymers useful as synthetic elastomers.

The olefinic products are converted to secondary and tertiary alcohols as by sulfuric acid-catalyzed hydration. Alternatively, the olefinic products are converted by conventional "Oxo" processes to aldehydes which are hydrogenated with conventional catalysts to the corresponding alcohols. The $C_{12}$–$C_{20}$ alcohols thereby produced are ethoxylated as by reaction with ethylene oxide in the presence of a basic catalyst, e.g., sodium hydroxide, to form conventional detergents and the lower molecular weight alcohols are esterified by reaction with polybasic acids, e.g., phthalic acid, to form plasticizers for polyvinyl chloride.

EXAMPLES

The olefins used in the following examples were commercial materials which were purified by contact with silica gel and were stored over 4 A molecular sieves before use. All the halogenated solvents and carbon tetrachloride were distilled from drying agents appropriate for the material and were stored over 4 A molecular sieves before use. The other halogenated activators were merely stored over 4 A molecular sieves under $N_2$ prior to use.

The carbene complexes were prepared by published procedures by reacting the appropriate metal compound with an organolithium compound followed by reaction with trimethyloxonium tetrafluoroborate. For example, tungsten hexacarbonyl was reacted with phenyllithium and was then reacted with trimethyloxonium tetrafluoroborate to form (methoxyphenylcarbene)pentacarbonyltungsten(O), viz.

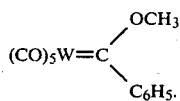

The carbene complexes were stored in a desiccator in a freezer before use in a reaction.

Each of the runs in the following examples was carried out in a 10 oz. beverage bottle equipped with a magnetic stirrer, and a self-sealing elastomeric liner in a three-hole crown cap. The liquid reaction components were charged to the dried, nitrogen flushed bottle by syringe through the cap. Solids were added to the bottle before attaching the cap. The reaction mixture was heated to the desired temperature and stirred at the reaction temperature for the desired time period. At the conclusion of the reaction time period, the reaction mixture was analyzed by gas-liquid chromatography (glc). The glc peak areas were converted to weights using an internal standard. Since 2 molecules of 1-pentene are disproportionated to 1 molecule of ethylene and 1 molecule of 4-octene, the yields of 4-octene are expressed as a mole percent yield based on one-half of the number of moles of 1-pentene charged to the reactor. The ethylene product was not determined and the 4-octene is a mixture of cis- and trans-isomers.

EXAMPLE I

Two control runs were carried out in the absence of the chlorinated or chlorobrominated hydrocarbon component of the present invention. In run 1, 1.54 g (22 mmoles) of 1-pentene and 4.4 ml of a solution of

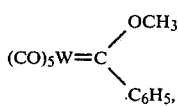

(0.11 mmoles) in chlorobenzene was charged to the reaction bottle. The mixture was stirred at room temperature (about 24° C.) for 24 hours. A glc analysis indicated that no reaction had occurred. The mixture was heated to 130° C. and stirred for 48 hours. Another glc analysis of the reaction mixture showed that no reaction had occurred.

In run 2, 1.54 g (22 mmoles) of 1-pentene, 4.4 ml of a solution of

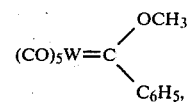

(0.22 moles) in hexane, and 10 ml of hexane were charged to the reaction bottle. The reaction mixture was stirred at 55° C. for 4 days. A glc analysis of the reaction mixture showed that no reaction had occurred.

The results of these runs show that neutral carbene complexes in the absence of activators are not effective for the disproportionation of olefins.

EXAMPLE II

A series of runs was carried out in which the disproportionation of 1-pentene was attempted in the presence of several halogenated hydrocarbons. In each run, 1.54 g (22 mmoles) of 1-pentene, 0.22 mmoles of

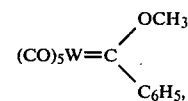

the halogenated hydrocarbon, and hexane were charged to the reaction bottle. The quantities of the halogenated hydrocarbon and hexane are given in Table I. Each run was carried out at 55° C. The reaction times and results are listed in Table I.

TABLE I

| Run No. | Halide, ml, mmoles | Other, ml | Reaction Time, Hrs. | Mole Ratio Halide/Carbene | 4-Octene Yield, Mole % |
|---|---|---|---|---|---|
| 3 | CCl$_4$, 0.02, 0.21 | Hexane, 7.4 | 96 | 1/1 | 0 |
| 4 | CCl$_4$, 0.3, 3.1 | Hexane, 4.4 | 23 | 14/1 | 0 |
| 5 | CCl$_4$, 0.64, 6.6 | Hexane, 14.4 | 96 | 30/1 | 39.6 |
| 6 | CCl$_4$, 5, 51.8 | Hexane, 4.4 | 24 | 235/1 | 16.4 |
| 7 | BrCCl$_3$, 0.3, 3 | Hexane, 14.4 | 20 | 13.6/1 | 13.2 |
| 8 | Cl$_3$CCCl$_3$, 0.71$^a$, 3 | Hexane, 14.4 | 72 | 13.6/1 | 47 |

$^a$grams

The results of runs 3 to 6 in Table I illustrate the critical nature of the level of carbon tetrachloride on the disproportionation of 1-pentene. At CCl$_4$/carbene mole ratios above about 15/1, disproportionation did occur. Runs 7 and 8 show that the carbene complex with either bromotrichloromethane or hexachloroethane catalyzes the disproportionation of 1-pentene. No evidence of any isomerization of the 1-pentene was observed except possibly in run 8.

EXAMPLE III

Several control runs were carried out with halogenated compounds outside the scope of the present invention. In each run, the reaction bottle was charged with 1.54 g (22 mmoles) of 1-pentene, 4.4 ml of a hexane solution of

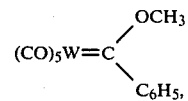

(0.22 mmoles), a halogenated compound, and hexane. The amounts of halogenated compound and total hexane present are shown in Table II. Each run was carried out at 55° C. The reaction times and results are shown in Table II.

TABLE II

| Run No. | Halide, ml | Hexane, ml | Reaction Time, Hrs. | 4-Octene Yield, Mole % |
|---|---|---|---|---|
| 9 | C$_6$H$_5$CCl$_3$, 0.42 | 14.4 | 20 | t* |
| 10 | CH$_2$Br$_2$, 1.54 | 7.4 | 48 | 0 |
| 11 | CHBr$_3$, 1.93 | 7.4 | 48 | t |
| 12 | CHCl$_3$, 5 | 9.4 | 20 | 0 |
| 13 | CH$_3$CCl$_3$, 0.3 | 9.4 | 20 | 0 |
| 14 | CBr$_4$, 1.0 | 24.4 | 72 | t |
| 15 | Cl$_3$C—CO—CCl$_3$, 0.46 | 9.4 | 96 | 3.6 |
| 16 | Cl$_3$C—C(Cl)=CCl$_2$, 0.42 | 9.4 | 96 | 1.7 |

*t = trace amounts of 4-octene.

The results in Table II show that halogenated compounds containing aryl groups (run 9), alipatic hydrogens (runs 10 to 13), only carbon and bromine (run 14), oxygen (run 15), or a carbon-carbon double bond (run 16) are much less effective than the chlorinated or bromochlorinated compounds used in the present invention in combination with carbene complexes for the disproportionation of olefins.

EXAMPLE IV

Three runs were carried out to evaluate the effect of the structure of the carbene complex on olefin disproportionation. In run 17, the reaction bottle was charged with 1.54 g (22 mmoles) of 1-pentene, 5 ml (52 mmoles) of carbon tetrachloride, and 8.8 ml of a hexane solution containing 0.22 mmoles of

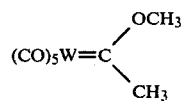

Note that this carbene complex contained a methyl radical attached to the carbene carbon in place of the phenyl radical used in the carbene complex in previous runs. The reaction mixture was heated at 55° C. for 22 hours. A glc analysis of the reaction product showed that 4-octene was formed in a yield of only 2.2 mole percent. The result of this run shows that when alkyl radicals are attached to the carbene carbon of the carbene complex, much less disproportionation occurs than when an aryl radical is attached to the carbene carbon.

In run 18, a carbene complex of the formula

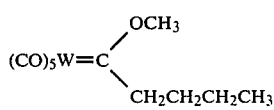

was employed. Again essentially no reaction occurred. This run provides additional evidence that superior results are obtained when there is an aryl radical attached to the carbene carbon of the complex.

In run 19, the reaction bottle was charged with 1.54 g (22 mmoles) of 1-pentene, 5 g (52 mmoles) of carbon tetrachloride, and 16 ml of a hexane solution containing 0.2 mmoles of

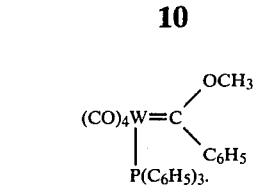

Note that this carbene complex contained a triphenyl phosphate group in place of one of the carbonyl groups of the carbene complex used in previous examples. The reaction mixture was heated at 55° C. for 96 hours. A glc analysis of the reaction product mixture showed that no 4-octene was present. The result of this run indicates that the presence of triphenyl phosphine ligands on the metal are detrimental to the disproportionation.

EXAMPLE V

Two runs were carried out with cyclic olefins as the starting materials for disproportionations in the presence of a carbene complex and hexachloroethane. In run 20, the reaction bottle was charged with 2.4 ml (27 mmoles) of cyclopentene, 4.4 ml of a solution of

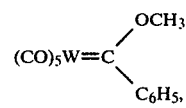

(0.22 moles) in hexane, 0.16 g (0.66 mmoles) of hexachloroethane, and 10 ml of hexane. The reaction mixture was stirred at 55° C. for 4 days. A glc analysis of the reaction mixture showed that essentially no reaction occurred. The result of this run shows that small cyclic olefins are not suitable starting materials for self-disproportionation with the catalyst system of this invention.

In run 21, the reaction vessel was charged with 2.42 g (22 mmoles) of cyclooctene, 4.4 ml of a solution of

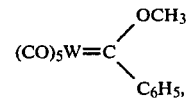

(0.22 mmoles) in hexane, 10 ml hexane, and 0.71 g (3 mmoles) of hexachloroethane. The reaction mixture was stirred at 55° C. for 96 hours. A glc analysis of the product mixture showed that about 94 percent of the cyclooctene had been reacted, but no new volatile products were observed. An infrared spectrum of the product after removal of the volatile materials shows the presence of cyclic olefins, thus demonstrating the process of this invention for the self-disproportionation of cyclooctene. An analysis of the product by GC-MS (gas chromatography-mass spectrum) indicated that a dimer was present. The dimer is a cyclohexadecadiene and is probably the 1,9-isomer from self-disproportionation of cyclooctene by analogy with published reports of the disproportionation of cyclooctene with other catalyst systems.

While particular embodiments of the present invention have been given for the purpose of illustrating the present invention, those examples should not be viewed as limiting the scope of the appended claims.

What is claimed is:

1. A catalyst composition consisting essentially of (1) at least one neutral carbene complex having the general formula

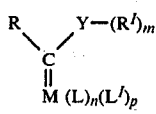

wherein R is an aryl or substituted aryl radical containing 6 to 30 carbon atoms per radical wherein the substituted aryl radical can have one or more substituents each of which can be the same or different and selected from the group consisting of halides, alkoxides and alkyl radicals containing 1 to 20 carbon atoms per radical; $R^I$ is selected from the group consisting of alkyl, cycloalkyl, aryl, substituted aryl, trialkylsilyl, and triarylsilyl radicals containing 1 to 30 carbon atoms per radical with the aryl substituents being the same as for the substituted aryl of R; Y is O, Se, S, N, or P; m is 1 when Y is O, Se, or S and 2 when Y is N or P; M is tungsten or rhenium; each L is individually selected from CO, NO, $PF_3$, $PCl_3$, or pyridine; $L^I$ is cyclopentadienyl or allyl; p is 0 or 1; and n is 5 when p is 0 or 2 when p is 1, and (2) at least one activator selected from chlorinated or chlorobrominated saturated organic compound having 1 to 20 carbon atoms per molecule and containing only carbon and chlorine or carbon, chlorine, and bromine, wherein said neutral carbene complex and said activator are present in such amounts as to have a catalytic effect upon the disproportionation of 1-pentene.

2. A catalyst composition according to claim 1 wherein the molar ratio of said activator to said carbene complex is in the range of about 1/1 to about 1000/1.

3. A catalyst composition according to claim 2 wherein R is a phenyl radical, Y is oxygen, M is tungsten, and $R^I$ is a hydrocarbyl alkyl radical containing 1 to 10 carbon atoms.

4. A catalyst composition according to claim 3 wherein said activator is selected from the group consisting of carbon tetrachloride, bromotrichloromethane, hexachloroethane, dibromodichloromethane, chlorotribromomethane, tribromotrichloroethane, octachloropropane, octachlorocyclobutane.

5. A catalyst composition according to claim 3 wherein said activator is selected from bromotrichloromethane, carbon tetrachloride, and hexachloroethane.

6. A catalyst composition according to claim 5 wherein $R^I$ is a methyl radical.

7. A catalyst composition according to claim 6 wherein said activator is carbon tetrachloride and the molar ratio of said activator to said carbene complex is in the range of about 20/1 to about 1000/1.

8. A catalyst composition according to claim 7 wherein the molar ratio of said activator to said carbene complex is in the range of about 30/1 to about 500/1.

9. A catalyst composition according to claim 6 wherein the molar ratio of said activator to said carbene complex is in the range of about 5/1 to about 100/1.

10. A catalyst composition according to claim 3 wherein said activator is selected from the group consisting of bromotrichloromethane, hexachloroethane, dibromodichloromethane, chlorotribromomethane, tribromotrichloroethane, octachloropropane, octachlorocyclobutane and wherein the molar ratio of said activator to said carbene complex is in the range of about 5/1 to about 100/1.

* * * * *